United States Patent [19]

Feres et al.

[11] Patent Number: 4,717,669
[45] Date of Patent: Jan. 5, 1988

[54] CENTRIFUGAL FILM FERMENTER

[76] Inventors: Vaclav Feres, Haid-und Neu-Strasse 14, 7500 Karlsruhe 1, Fed. Rep. of Germany; Rudolph V. Roubicek, 1304 Delano, Las Cruces, N. Mex. 88001

[21] Appl. No.: 897,350

[22] Filed: Aug. 18, 1986

[51] Int. Cl.$^4$ .............................................. C12M 1/06
[52] U.S. Cl. .................................... 435/315; 435/313; 435/316; 261/89
[58] Field of Search ............... 435/315, 313, 316, 310, 435/312; 261/89, 83, 85, 88, 90; 210/175, 178, 183, 927

[56] References Cited

U.S. PATENT DOCUMENTS

| | | | |
|---|---|---|---|
| 2,983,652 | 5/1961 | Baerfuss | 435/315 X |
| 3,616,260 | 10/1971 | Müller | 435/316 X |
| 3,962,042 | 6/1976 | Malick | 435/315 X |
| 4,263,143 | 4/1981 | Ebner et al. | 435/315 X |
| 4,339,398 | 7/1982 | Feres | 261/89 |
| 4,446,236 | 5/1984 | Clyde | 435/813 |

FOREIGN PATENT DOCUMENTS 153109 11/1920 United Kingdom ................. 261/89

Primary Examiner—Larry Jones
Attorney, Agent, or Firm—Milton D. Wyrick

[57] ABSTRACT

Fermentation equipment is provided with multiple rotating conical surfaces which create a flow of the liquid phase along the conical surfaces and produce a forced flow of the gaseous phase across the liquid phase, thus resulting in much improved mass transfer between the phases and preventing the formation of foam. The equipment is provided within a standard sterilizable fermentation vessel at the bottom of which is located propeller means for circulation of the liquid phase, cylindrical heat exchanger means for heating or cooling the liquid phase and a gas sparging system for introduction of the gaseous phase.

7 Claims, 2 Drawing Figures

CENTRIFUGAL FILM FERMENTER

FIELD OF INVENTION

The present invention relates to fermenter equipment to be used in the laboratories, in pilot plants, and in large scale industrial anaerobic and anerobic processes and which is applicable for cultivation of living cells, for production of primary or secondary metabolites, for photosynthesis and for combined processes involving photosynthesis in conjunction with an anaerobic process.

CROSS-REFERENCE TO RELATED PATENTS

Roubicek, R. V., Feres, V., "Equipment for Enhanced Mass Transfer and Defoaming in Chemical and Biological Processes," U.S. Pat. No. 4,657,677, issued Apr. 14, 1987.

BACKGROUND OF THE INVENTION

Conventional equipment for the fermentation and propagation of micro-organisms generally consists of a vessel equipped with means for introducing gases such as oxygen, air, or carbon dioxide into the fermentation liquor, and a motor-driven mechanical mixing means to provide intense agitation. This agitation creates a large quantity of bubbles of the gaseous phase within the fermentation liquor, thus facilitating the molecular transport between the gaseous phase and the fermentation liquor. Typical mechanical mixing means consist of various designs of impellers to achieve efficient distribution of the gaseous phase into the fermentation liquor and to provide adequate flow characteristics of the liquid nutrient medium which is necessary for the physiology of the cultivated plant or animal cells. The mass transfer capabilities of such equipment can be improved by such modifications by the use of baffling systems, draft tubes, or air lift methods.

However, each of these conventional methods requires a great deal of mechanical energy to distribute the gaseous phase through the liquid phase and to provide the necessary mixing in large industrial scale equipment, resulting in both technical and economic problems. In addition to the high energy consumption of these systems, the mechanical agitation of the fermentation liquor in many fermenters creates high shear stresses on the cells which limit or inhibit cell growth.

Another problem with conventional fermenters concerns foaming. In prior art systems, the introduction of large quantities of gas into the vigorously agitated fermentation liquor often produces great quantities of foam in the reaction vessel. This foam severely limits the usable volume of the vessel and can render the fermentation process inoperable and microbially contaminated when the gas flow exit lines become filled with foam. All of these problems have a substantially adverse influence upon the yield an cost-effectiveness of conventional fermentation processes.

Numerous chemical and mechanical devices have been proposed to solve the foaming problem in industrial biosynthesis processes. Most of the existing methods are founded upon chemical or mechanical defoaming of a developed foam. Chemical treatment currently used for defoaming involves silicones and other water-immiscible additives which substantially decrease the rate of oxygen transfer, thus interfering with an effective process of aerobic biosynthesis. The mechanical defoamers which are sometimes used in fermentation processes typically require an additional power source and a particular fermenter design to accommodate the defoaming equipment. Mechanical defoamers are not uniformly reliable or feasible, especially in large fermentation vessels. In summary, the disadvantages of the prior art procedures for mass transfer in aerobic processes are as follows: high cost of mixing and aeration, heavy foaming, high shear stress on cells, and frequent incidents of contamination in aerated systems. These difficulties, all in their own way, interfere with the efficiency and economy of the fermentation processes.

Devices which eliminate or greatly diminish some of the above disadvantages of the prior art have been described in previous U.S. Pat. No. 4,339,398, to Feres, one of the inventors herein, and in the related U.S. Pat. No. 4,657,677, to the applicants herein. The equipment disclosed in the related application is for improved mass transfer achieved by generating a thin film of liquid which flows upward along a rotating truncated conical surface, exposing a large area of flowing liquid to a substantially static, gaseous phase. This equipment is useful in promoting efficient molecular transfer of gases with a low solubility in the liquid, for example the transport of oxygen into an aqueous phase, typical of conventional aerobic fermentation processes. The principle of this system can alternately be employed in the reverse direction of transfer, as is with gases leaving a liquid phase, such as occurs in stripping, defoaming, and deodorization. An important feature of this equipment, like the present invention, is the fact that the thin-film process prevents the formation of foam, a serious problem with prior art fermentation processes. Traditional prior art methods of foam control have been directed toward control of existing foam, not toward preventing the formation of foam.

It is desirable to produce equipment to efficiently and economically, from both an energy and process effectiveness standpoint, carry out fermentation processes. It is also desirable to produce a fermenter which is substantially free from microbial contamination and in which the process itself prevents the formation of foam. It is still further desirable to produce a fermenter which does not subject cells and organisms to high shear stress.

These and other undesirable problems of the prior art are overcome by the present invention and improved equipment for carrying out the fermentation process is provided.

SUMMARY OF THE INVENTION

To achieve the foregoing and other objects, and in accordance with the purposes of the present invention, as embodied and broadly described herein, the apparatus of this invention may comprise a typical sterilizable fermentation vessel on the top of which drive means are flange mounted and connected to a central shaft which is further attached to a central distributor. The central distributor is open at its lower end and may have fixedly attached to it and rotating with it a plurality of conical surfaces or alternatively, have the cones spaced a short distance away, and attached one to the other and to drive means. Below the central distributor, a cylindrical heat exchanger is provided, having an axially mounted propeller, operated by drive means, located at its lower end. With the central distributor rotating and having its lower end submerged in the liquid phase, liquid is drawn up along the inner surface of the central distributor and ejected through a set of openings and distributed onto the rotating conical surfaces. Simultaneously, a flow of gas over the thin liquid film on the conical surfaces is created by the same centrifugal force which is moving the liquid along the conical surface. When the cones are attached to the central distributor, this gas flow is through nozzles in the central distributor which are so arranged to prevent the ingress of liquid. These nozzles create a forced flow of the gaseous phase across the thin film of flowing liquid. When the cones are spaced apart from the central distributor, the gas flow is between the cones and the central distributor.

The flow of the liquid phase to the inlet of the central distributor is enabled by raising the liquid level within the heat exchanger cylindrical guide tube by operation of the axial propeller pump. The flow to the central distributor can be controlled by varying the level of the liquid in the heat exchanger tube, or by adjusting the vertical position of the central distributor. When desired, the gaseous phase is supplied at the bottom of the fermenter through a gas sparging system, contributing to the versatility of the fermenter equipment.

DETAILED DESCRIPTION OF THE INVENTION

Figure 1:
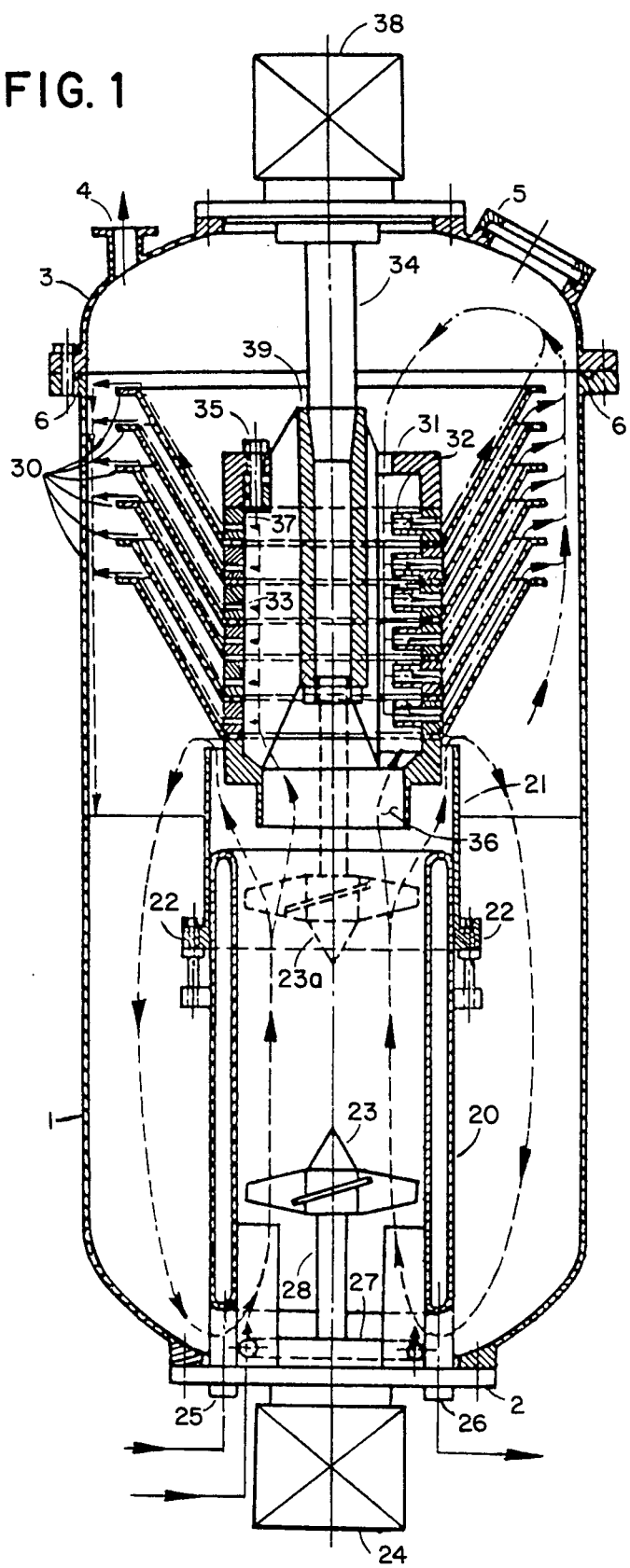
FIG. 1 is a longitudinal cross section through the preferred embodiment of the invention.

The centrifugal film fermenter is shown as a modified longitudinal cross section in FIG. 1 and comprises vessel 1, vessel bottom 2, and vessel lid 3. Both vessel bottom 2 and vessel lid 3 are flanged to vessel 1 and sealed thereto by O-rings 6. Vessel lid 3 contains sight glass 5 and gas outlet 4. Further, central distributor drive means 38 is mounted to vessel lid 3 and drive shaft 34, which is mechanically double sealed, and extends through vessel lid 3 into the interior of vessel 1. Hub 39 of drive shaft 34 is connected to the central distributor 31, comprising a stacked arrangement of conical surfaces 30 which are supported by the central distributor 31 and are centered and are spaced apart, one from the other, by central distributor rings 37. Each central distributor ring 37 comprises a plurality of liquid inlet apertures 33 and gas inlet nozzles 32. The bottom of the central distributor contains a ring with an opening 36 for liquid intake into central distributor 31.

Axially aligned with central distributor 31, but not connected thereto is cylindrical heat exchanger 20, which is fixedly mounted to vessel bottom 2. Heat exchanger 20 is a double-walled cylinder, allowing a heating or cooling medium to circulate therethrough by way of heat exchanger medium inlet 25 and heat exchanger medium outlet 26. Near the top of heat exchanger 20 is mounted cylindrical regulator 21, whose inside diameter is only slightly larger than the outside diameter of heat exchanger 20. Cylindrical flow regulator 21 is raised and lowered along heat exchanger 20 by flow regulator adjustment means 22, providing control of the level of liquid in the heat exchanger 20.

A variable speed drive means 24 is mounted to vessel bottom 2 and connected to propeller 23 through shaft 28. A gas sparging system 27 can be mounted near the upper surface of vessel bottom 2. If desired, only distributor drive means 38 would be necessary if propeller 23a were connected to the drive shaft 34 of central distributor 31. This alternate position of propeller 23a is shown by broken lines.

In operation, the liquid phase, being a sterilized, temperature adjusted and innoculated nutrient medium, is pumped in an upward direction by action of the axial propeller 23, through cylindrical heat exchanger 20, where it is either heated or cooled. According to the spacing between cylindrical flow regulator 21 and the lower surface of the bottom-most conical surface 30, a portion of the liquid phase enters central distributor 31 through central distributor opening 36 and the remainder is returned to the bottom of vessel 1 to be recirculated through heat exchanger 20.

The portion of the liquid phase which enters central distributor 31, which is rotating through the action of drive means 38, is drawn by centrifugal forces upward along the inner surface of central distributor rings 37. These central distributor rings 37 maintain the proper spacing between the conical surfaces 30 and fix them in place, and contain, at intervals along their inner periphery, gas inlet nozzles 32 and liquid inlet apertures 33. The apertures 33 have diameters varying from smallest at the lower section of central distributor 31 and become progressively larger higher in central distributor 31, thus equalizing the liquid flow to the rotating conical surfaces 30. The liquid phase then proceeds along the conical surfaces 30 until it is flung from the conical surface against the wall of vessel 1 to return to be recirculated. The gas inlet nozzles 32 serve to inject the gaseous phase onto the conical surfaces 30 and to propel the gaseous phase at a high velocity above the much slower thin film flow of the liquid phase thus enhancing mass transfer. The inlets for the nozzles 32 are spaced away from the inner periphery of the central distributor rings 37 to prevent entry of the liquid phase. The velocity gradient created by the respective flows of the liquid and gaseous phases along the surfaces of the conical surfaces 30, greatly enhances the molecular transfer of the gaseous phase into the liquid phase. This molecular transfer is far superior to conventional agitation fermenters and is even superior to our previous inventions related to rotating conical surfaces, where, although the liquid phase is moving along the cones, the gaseous phase is substantially stagnant. Similarly, as in our previous invention, the design of the conical surfaces might be either flat, corrugated, baffled or scooped to change the characteristics of the fluid flow. In FIG. 1 the flow of the liquid phase is marked by uniformly broken lines, while the flow of the gaseous phase is marked with dot-dash lines. From these lines it is seen how part of the liquid phase flows through cylindrical flow regulator 21 and along central distributor rings 37, through the liquid inlet apertures 33, along conical surfaces 30 and back to the inlet of the cylindrical jacketed heat exchanger 20. A second part of the liquid phase passes out the top of the flow regulator 21 back to the inlet of the cylindrical jacketed heat exchanger 20. It is also seen how the gaseous phase is drawn into central distributor 31, through gas inlet nozzles 32, along the surface of the liquid flow on conical surfaces 30 and then back to central distributor 31.

The provision of gas sparging system 27 below propeller 23 provides a supplemental flow of the gaseous phase, further enhancing the mass transfer between liquid and gas making the fermenter useful in many different processes, including biological and chemical processes based on a transport operation. Further, photosynthetic processes can be carried out if illumination is added to the upper portion of vessel 1. With such illumination, the invention can be used to produce pure methane gas, where an anaerobic process at the bottom is used to evolve carbon dioxide, which is then utilized as the carbon source for photosynthesis.

Still further, anaerobic processes may be practiced by the invention, by using an inert gas phase which is oxygen free.

Figure 2:
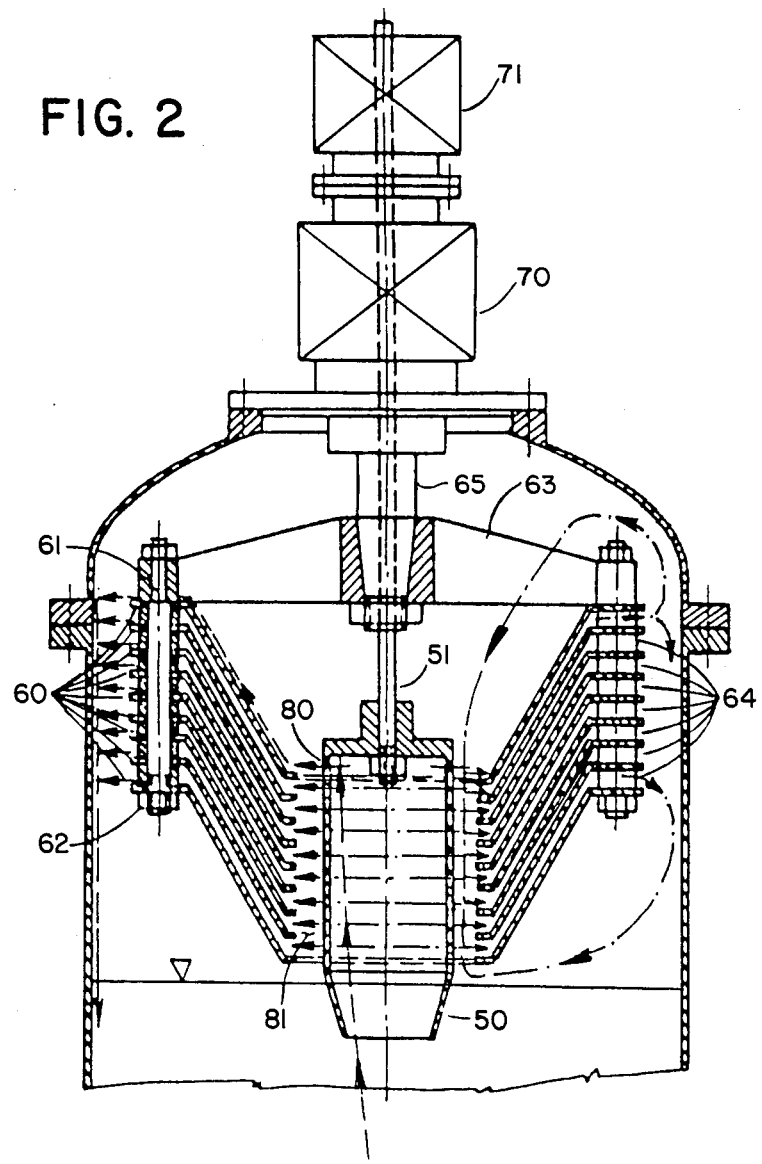
FIG. 2 is a longitudinal cross section of an alternative arrangement of the central distributor and conical surfaces.

Referring now to FIG. 2, an alternative arrangement for the upper section of the apparatus shown in FIG. 1 is shown distinguished by the fact that there is no longer a direct contact between central distributor 50 and the conical surfaces 60. Instead, said conical surfaces 60 are fixed by bolts 61 and nuts 62 to support beam 63. Individual conical surfaces 60 are fixed in a spaced-apart position by washers 64. Support beam 63 is attached through shaft 64 to rotation mean 70.

Central distributor 50 is attached through shaft 51 to rotation means 71. This arrangement allows the central distributor 50 to rotate at a velocity different from that of the conical surfaces 60. If this feature is not required, a single rotation means could be employed.

Central distributor 50 has numerous openings 80 through its sides which permit the liquid phase flowing up the inner surface of central distributor 50 to flow out across air gap 81 and onto the adjacent conical surface 60. Air gap 81 permits gases to flow from both the top and bottom of conical surfaces 60.

It should be noted that the sidewalls 31 of central distributor 50 need not be vertical, but that the shape may be varied, such as into the form of a parabola, to obtain the desired liquid flow characteristics. Further, in either embodiment, the central distributor 31 or 50 can be adjusted vertically within the liquid phase, allowing variances of the rate with which the liquid flows through central distributor 31 or 50.

The foregoing description of the preferred embodiments of the present invention has been presented for purposes of illustration and description. It is not intended to be exhaustive or to limit the present invention to the precise forms disclosed. Obviously, many modifications are possible in light of the above teaching. The embodiments were chosen and described in order to best explain the principles of the present invention and its practical applications to thereby enable others skilled in the art to best utilize the present invention in various embodiments and with various modifications as are suited to the particular use contemplated. It is intended that the scope of the present invention be defined by the claims appended hereto.

We claim:

1. A centrifugal film fermenter comprising:
   a closed sterilizable fermentation vessel;
   rotatable distributor means disposed axially within said vessel comprising a plurality of perforations to facilitate the flow of liquids and gases therethrough;
   two or more truncated conical surfaces fixedly attached to said distributor means and located adjacent to said perforations so as to accept said flow of liquids and gases;
   rotation means connected to said distributor means through central shaft means;
   cylindrical heat exchange means disposed below said distributor means, and comprising heat exchange medium inlet and outlet means;
   cylindrical flow regulator means slidably engaged with the outer surface of said heat exchange means through height adjustment means;
   one or more propeller means disposed within said cylindrical heat exchanger means and connected through a shaft to rotatation means;
   gas sparging means disposed within said heat exchange means having its outlet inside said vessel and its inlet extending through said vessel to its outer surface.

2. A centrifugal film fermenter as described in claim 1, wherein said distributor means comprises apertures through its vertical surface for the passage of liquid and nozzles through its vertical surface for the passage of gases.

3. A centrifugal film fermenter as described in claim 1, wherein means for illumination are provided at the top of said vessel for the practice of photosynthetic processes.

4. A centrifugal film fermenter comprising:
   a closed, sterilizable fermentation vessel;
   distributor means disposed axially within said vessel, comprising a plurality of perforations to facilitate the flow of liquid and gas therethrough;
   two or more truncated conical surfaces connected to central shaft means and spaced apart from said distributor means, but, with located adjacent to said perforations to accept said flow of liquids and gases;
   rotation means connected to said central distributor through central shaft means;
   cylindrical heat exchange means disposed below said distributor means and comprising heat exchange medium inlet and outlet means;
   cylindrical flow regulator means slidably engaged with the outer surface of said heat exchange means through height adjustment means;
   one or more propeller means disposed within said heat exchange means and connected through shaft means to rotation means;
   gas sparging means disposed within said heat exchange means comprising an outlet within said vessel and an inlet extending through the surface of said vessel.

5. The centrifugal film fermenter as described in claim 4 wherein said rotation means comprises a separate motor for said distributor means, a separate rotation means for said truncated conical surfaces and a separate rotation means for said propeller means.

6. The centrifugal film fermenter as described in claim 4 wherein said distributor means and said central shaft means are vertically adjustable.

7. The centrifugal film fermenter as described in claim 1 or 4, wherein said propeller means is fixedly attached to said central shaft means.

* * * * *